United States Patent [19]

Jackson

[11] 4,342,315

[45] Aug. 3, 1982

[54] SUCTION CATHETERS WITH IMPROVED SUCTION CONTROL VALVE

[75] Inventor: Isaac S. Jackson, Greenwich, N.Y.

[73] Assignee: Mallinckrodt, Inc., St. Louis, Mo.

[21] Appl. No.: 37,878

[22] Filed: May 10, 1979

[51] Int. Cl.³ .................. A61M 25/00; A61M 1/00
[52] U.S. Cl. ............................. 128/349 R; 128/276;
128/274; 433/95
[58] Field of Search ............... 119/1; 251/342, 4, 341;
128/350 V, 349 BV, 274, 276, 764, 240, 239,
349 R, 350 R, 350 V; 433/95, 96

[56] References Cited

U.S. PATENT DOCUMENTS

| | | | |
|---|---|---|---|
| 274,447 | 3/1883 | Kennish | 251/342 |
| 478,872 | 7/1892 | Kirkwood | 128/240 |
| 2,147,652 | 2/1939 | Kennison | 128/240 |
| 2,755,060 | 7/1956 | Twyman | 251/342 |
| 2,969,066 | 1/1961 | Holter et al. | 128/350 V |
| 3,645,497 | 2/1972 | Nyboer | 433/95 |
| 3,654,932 | 4/1972 | Newkirk et al. | 128/274 |
| 3,675,658 | 7/1972 | Taylor | 128/349 BV |

FOREIGN PATENT DOCUMENTS

| | | | |
|---|---|---|---|
| 35387 | 11/1965 | German Democratic Rep. | 128/274 |
| 346330 | 2/1937 | Italy | 128/240 |

Primary Examiner—Henry J. Recla
Assistant Examiner—J. L. Kruter

[57] ABSTRACT

Suction catheters are provided with improved suction control valves that have no open ports and that are normally closed providing advantages over the conventional control valves that are normally open. The valve comprises a resilient member having a distal end of chisel point design that is slit at the tip enabling the slit to be pinched open through an enveloping sheath to apply suction to the catheter and return to a closed position upon release of pinch pressure. The catheter may include vents to release vacuum if its distal end openings become occluded.

8 Claims, 11 Drawing Figures

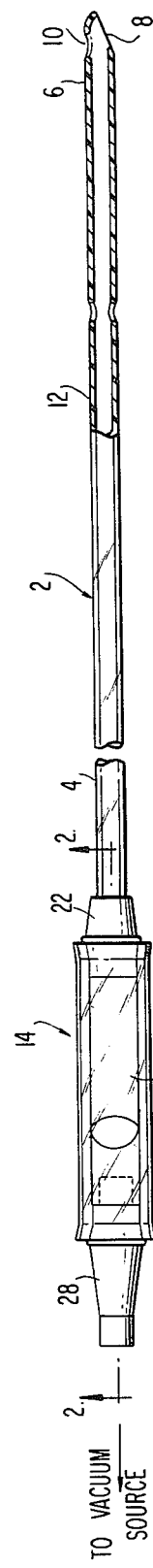

SUCTION CATHETERS WITH IMPROVED SUCTION CONTROL VALVE

BACKGROUND OF THE INVENTION

1. Field of the Invention

This invention relates to suction catheters and suction control valves therefor. More particularly, it relates to on/off valves for suction catheters that are normally closed, but which may be opened for application of vacuum by mere pinching of a valve member.

2. Description of the Prior Art

Suction catheters are extensively used during surgical operations and in post-operative care for aspiration of mucus, blood and other fluids from nose, mouth, pharynx, trachea, bronchi, stomach or other cavities of the patient's body (see U.S. Pat. Nos. 3,848,604; 3,945,385 and 3,965,901).

Since the control of suction, either in extent of time or degree of vacuum may be required during use of suction catheters, it is conventional to provide such catheters, either as an integral unit or as an optional attachment, with suction control valves (see U.S. Pat. Nos. 3,375,828; 3,595,234 and 3,610,242).

Although internal valves for tubes that are of the normally closed type are known (see U.S. Pat. No. 274,447), it has been considered advisable in the past, for ease and accuracy of control, to use suction control valves of the normally open type with suction catheters. However, the known present open-port control valve suction catheters and Yankauer suction devices involve some disadvantages. Obviously, an open port wastes vacuum potential continuously. Also, the open port exposes the user to fluids that may spatter through the open port and present a source of possible cross infection. Depending on the level of vacuum used, the open port can create annoying hissing or sputtering noises. Additionally, since an open port type control may allow residual vacuum pressure at a catheter tip even when the port is "full open", there can be a tendency to evacuate air from a body cavity, e.g., the lungs, with the control port full open. Some users kink the sunction tube before introduction to guard against this problem.

Notwithstanding the numerous improvements that have been made in the past in the art of medico-surgical tube devices, including suction catheters and their control valves, there is need for further improvements to eliminate problems of use and design associated with such devices. Of course, if such improvements are to be effective, they should not introduce other problems or disadvantages that would negate their adoption and use by the trade.

OBJECTS

A principal object of the present invention is the provision of new improvements in suction control valves for medico-surgical tube devices and suction catheters incorporating such valves.

Further objects include the provision of:

(1) Control valves for suction catheters that are normally closed, i.e., open the suction line to fluid flow only when the catheter user needs to "suction".

(2) Such control valves that have no open port to the full vacuum potential at the vacuum source is available when the valve is open and the valve does not require catch-up lag in response time.

(3) Improved suction control valves that a user can position in his hand simply by feeling orientation markings, thereby permitting "no look", one hand operation.

(4) Suction catheter control valves that eliminate an open port, therefore, lessening cross-infection conditions and mitigating disturbing noises caused by moving air, mucus or other fluids.

(5) Improved suction catheters designed so that when suctioning, if the tip is occluded by tissue, vacuum can be relieved distally of the control valve even in the valve closed position to release tissue holding by the catheter tip and avoid damage to the tissue should the suction catheter be withdrawn.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

These objects are accomplished according to the present invention by the provision of improved suction control valves for medico-surgical tube devices that have no open ports and until actuated by pinching by the user are in a normally closed condition. An essential element is a valve member of tubular configuration having a distal end of chisel point design that is slit at the tip so the slit may be pinched normal to its axis to open the valve to apply vacuum to an attached suction catheter.

The valve member is made of resilient material and is contoured so that the slit will close upon release of pinch pressure by the user. Such contouring preferably includes a controlled thickening of the valve member in the region of the chisel point.

The control valve further includes a flexible tubular member that envelopes the slit valve member together with means to attach a suction catheter at the distal end and rigid connector means on the proximal end. Preferably the flexible tubular member has protrusions on its outer surface to serve as indicators for positioning the valve in the hand of a user.

Advantageously, the improved suction control valves are used with suction catheters that include vent means to release vacuum if the distal end opening thereof became occluded. Such vent means may be very small side ports in the catheter or a unique vent associated with a secondary lumen in the wall of the catheter.

BRIEF DESCRIPTION OF THE DRAWINGS

A more complete understanding of the present invention may be had by reference to the accompanying drawings in which:

FIG. 1 is a fragmented, lateral view, partially in section, of a new suction catheter of the invention.

FIG. 2 is a fragmentary, enlarged sectional view taken on the line 2—2 of FIG. 1.

FIG. 3 is an enlarged, sectional view taken on the line 3—3 of FIG. 2.

FIG. 3A is a sectional view corresponding to FIG. 3, but with the valve in an opened position.

FIG. 4 is an enlarged, sectional view similar to FIG. 2 but with the valve in an opened position as in FIG. 3A.

FIG. 5 is a lateral elevation of a valve member of the new suction control valves of the invention.

FIG. 6 is an anterior elevation of the valve member of FIG. 5.

FIG. 7 is a sectional view taken on the line 7—7 of FIG. 5.

FIG. 8 is an anterior elevation of another form of valve member of the invention.

FIG. 9 is an enlarged fragmentary lateral view, partially in section, of another form of suction catheter of the invention.

FIG. 10 is a sectional view taken on the line 10—10 of FIG. 9.

FIG. 11 is a sectional view of another embodiment of catheters of the invention.

DESCRIPTION OF THE PREFERRED EMBODIMENTS

Referring in detail to the drawings, the suction catheter 2 comprises a proximal end 4, a distal end 6 having a whistle tip 8 and side port 10, a central portion 12 integrally uniting the proximal end 4 with the distal end 6 and a suction control valve 14 attached to the proximal end 4.

The valve 14 comprises a flexible tubular member 16 having a lumen 18 larger than the lumen 19 of the catheter 2. The proximal end 4 of the catheter is joined to the distal end 20 of the member 16 by the hub 22, preferably by cementing the proximal end 4 to the bore 24 of the hub 22 and the distal end 20 of member 16 to the proximal taper 26 of hub 22. The hub 22 may be provided with a rib 27 to limit the distance the end 26 extends into the end 20 of member 16.

The rigid connector member 28 with a lumen 30 smaller than the lumen 18 of member 16 has its distal end 32 fitted into the proximal end 34 of member 16 leaving the tapered proximal end 36 free for connection with a vacuum hose or other vacuum source (not shown). The distal end 32 of connector member 28 has an integral nipple 38 and a rib 39 may be provided to limit the distance the end 32 extends into the end 34 of member 16.

The valve member 40 comprises a proximal tubular portion 42 having a lumen 44 larger than the lumen 30 of connector member 28, but smaller than the lumen 18 of member 16, and a closed distal end portion 46 integral with the proximal portion 42. The free end 48 of valve member 40 is fitted over the nipple 38 and the two are preferably cemented together.

The closed distal portion 46 of valve member 30 is of chisel point design having a V-shaped (inverted) lateral cross-section 50 (see FIGS. 2 and 5) and a U-shaped (inverted) anterior cross-section 52 (see FIG. 7). The lateral cross-section 50 has a median slit 54 through it. Preferably, the lateral cross-section 50 tapers down in thickness from the apex 56 to the base, i.e., the distal portion 46 is radiused to thicken in the center. In the embodiments shown in FIGS. 5–7, the tip or apex 56 is also radiused.

In another embodiment, as shown in FIG. 8, the tip 56a of valve member 40a is straight (square).

The tubular member 16 has diametrically opposed longitudinal ribs 60 on the outer surface 62 to serve as indicators for the application of pressure as indicated by the arrows in FIG. 3A. Other types of protrusions, e.g., beads, spots, etc. can be used instead of ribs.

The various parts of the new control valves and catheters can be produced from any suitable materials and by a suitable method known to the art. Advantageously, the catheter 2 and member 16 are formed of plasticized polyvinyl chloride by extrusion, but other materials, e.g., polyolefins, rubber, silicone rubber, etc. and other methods, e.g., dip casting, molding, etc. may be used. Advantageously, the catheter 2 and member 16 are made of transparent material to provide see through ability. The hub 22 and connector member 28 should be formed of rigid material, e.g., nylon, polyethylene, PVC, hard rubber, etc., advantageously by injection molding, although other materials or methods may be used. The valve member 40 can be made of resilient material, e.g., silicone rubber, plasticized PVC, natural rubber, etc. and may be formed by contour molding, plastisol casting, blow molding, injection molding, etc.

Since the control valve 14 completely seals off the catheter 2 when in the closed position (see FIG. 2), it is possible when suctioning, if the ports 8 and 10 were to be occluded by tissue and the valve was closed by the user, that vacuum would remain in the catheter 2 and therefore "hold" the occluding tissue. If the user were to withdraw the catheter while the tip was holding tissue, damage to it could occur. In order to prevent this, a preferred form of the new catheters includes vent means in the distal end to automatically release vacuum in the catheter on the closing of the control valve. A preferred form of such new catheter is shown in FIG. 9.

The catheter 70 has a side-entering port 72 in the distal end portion 74. In addition to the primary lumen 76, there is a secondary lumen 78 within the catheter wall 80. This lumen 78 opens at its distal end 82 into the port 72 and at its proximal end 84 it opens through the outer surface 86 of the catheter wall 80 proximal of the port 72, e.g., about 10 cm. from the port 72. Alternatively, the opening 84 for the secondary lumen 78 could be in the vicinity of the catheter proximal end 88 so that it would vent outside the body of the patient. It is preferred, however, to have the opening 84 located so that it will be within the body of the patient when the catheter 70 is fully installed. The opening 84 to secondary lumen 78 would permit venting of the catheter within the trachea or one of the principal bronchi of the patient.

The catheter of FIG. 9 is equipped with a control valve 14 as described for the catheter 2. Upon closing of the valve 14, any vacuum remaining in the catheter 70 will be released by the venting action of the secondary lumen 78.

An alternative form of venting means is shown in FIG. 11. Here, the catheter 90 has tiny holes 92, e.g., holes 0.1 to 1 mm. diameter, through wall 94. Such holes will be positioned proximal of the catheter distal end similar to the positioning of openings 84 as described above. Hence, upon closing of the control valve 14 of the catheter, the lumen 96 of catheter 90 will be vented to ambient atmosphere and any residual vacuum created by occlusion of the distal end openings of the catheter will be released.

The control valves of the invention may be marketed as separate items for attachment to suction catheters. However, since the catheters are primarily designed to be disposable after a single use, the catheters and control valves are advantageously made and sold as single units. They may be made by automatic assemble methods in all the sizes and lengths required by the medical profession. The catheters are advantageously packaged in paper or plastic envelopes that permit them to be sterilized after packaging such as by exposure to ethylene oxide gas or gamma rays. If desired, the catheters may have a frosted slip surface (see U.S. Pat. No. 3,508,554).

The catheters 2 and 70 of FIGS. 1 and 9 have been shown as having a so-called whistle tip. The invention can be applied to suction catheters having any other type of tip found useful in the trade, e.g., closed end tips with side entering ports, squared-off tips with rounded edges or other acceptable tip structures.

The new control valves and catheters can operate effectively with vacuums from about 50 to 500 mm. Hg. The catheters will have zero negative pressure with the control valves in the normally closed position. Since the control valves have no open ports, they prevent soiling of a user's hand and also conserve vacuum potential. The pinch technique for operation is easily used and permits one hand manipulation. Moreover, the new suction catheters operate without the noise disturbances of the conventional open port control types.

The embodiments of the invention in which an exclusive property or privilege is claimed are defined as follows:

1. A suction catheter assembly with a lumen having a proximal end, a ported distal end, a suction control valve assembly portion connected to the proximal end of the catheter, said suction control valve assembly comprising:
    an elongated flexible tube having a proximal end, a distal end and a lumen larger than the lumen of the catheter connected to said valve,
    means connecting the distal end of said flexible tube to the proximal end of said catheter,
    a rigid connector member having a proximal end, a distal end and a lumen smaller than the lumen of said flexible tube fitted into the proximal end of said flexible tube with its distal end positioned within and its proximal end positioned without said flexible tube,
    the distal end of said rigid connector member bearing an integral nipple, and
    a valve member comprising a proximal tubular portion having a lumen larger than the lumen of said rigid connector member, but smaller than the lumen of said flexible tube, and a closed distal portion integral with the proximal tubular portion,
    the free end of said proximal tubular portion being fitted over said nipple and extending into said flexible tube,
    said closed distal portion being of a chisel point design having a V-shaped lateral cross-section and a U-shaped anterior cross-section, said lateral cross-section having a median longitudinal slit therethrough,
    said valve member being formed of resilient material permitting said V-shaped lateral cross-section to be parted along said median slit by application of pressure upon said valve member in a direction perpendicular to the longitudinal axis of said slit and to be restored to its close position upon release of said pressure,
    said flexible tube having protrusions on its outer surface positioned on said axis of said median slit to serve as indicators for application of pressure to open said valve member.

2. An improved suction catheter assembly of claim 1 wherein said V-shaped lateral cross-section tapers down in thickness from the apex thereof toward the base.

3. An improved suction catheter assembly of claim 1 wherein the distal edge of said lateral cross-section of said valve member is a substantially straight line.

4. An improved suction catheter assembly of claim 1 wherein the distal edge of said lateral cross-section of said valve member is an arcuate line.

5. An improved suction catheter assembly of claim 1 wherein said protrusions are raised lines.

6. An improved suction catheter assembly of claim 1 wherein said means for joining the distal end of said tubular member to the proximal end of said catheter comprises a hub into which the proximal end of the catheter is cemented and the proximal end of the hub is cemented in the distal end of said flexible tubular member.

7. A suction control valve for a medico-surgical tube device comprising:
    an elongated flexible tube having a proximal end, a distal end and a lumen therethrough,
    a rigid connector member having a lumen smaller than said lumen of said flexible tube fitted into the proximal end of said flexible tube, the distal end of said connector member being positioned within and its proximal end being positioned without said flexible tube,
    the distal end of said rigid connector member bearing an integral nipple, and
    a valve member comprising a proximal tubular portion having a lumen larger than the lumen of said rigid connector member, but smaller than the lumen of said flexible tube, and a closed distal portion integral with the proximal tubular portion,
    the free end of said proximal tubular portion being fitted over said nipple and extending into said flexible tube,
    said closed distal portion being of a chisel point design having a V-shaped lateral cross-section and a U-shaped anterior, cross-section, said lateral cross-section having a median longitudinal slit therethrough,
    said valve member being formed of resilient material permitting said V-shaped lateral cross-section to be parted along said median slit by application of pressure upon said valve member in a direction perpendicular to the longitudinal axis of said slit and to be restored to its closed position upon release of said pressure.

8. The suction control valve of claim 7 wherein said flexible tube has protrusions on its outer surface positioned on said axis of said median slit to serve as indicators for application of pressure to open said valve member.

* * * * *